US00PP11170P

United States Patent [19]

Zary

[11] Patent Number: Plant 11,170

[45] Date of Patent: Jan. 4, 2000

[54] FLORIBUNDA ROSE PLANT NAMED 'JACQUINT'

[75] Inventor: Keith W. Zary, Thousand Oaks, Calif.

[73] Assignee: Bear Creek Gardens, Inc., Medford, Oreg.

[21] Appl. No.: 09/024,352

[22] Filed: Feb. 17, 1998

[51] Int. Cl.[7] ..... A01H 5/00

[52] U.S. Cl. ..... Plt./148

[58] Field of Search ..... Plt./148

*Primary Examiner*—Howard J. Locker

*Attorney, Agent, or Firm*—Klarquist Sparkman Campbell Leigh & Whinston, LLP

[57] ABSTRACT

Floribunda rose plant having large flowers of strong fragrance, vigorous growth, compact plant habit and disease resistant foliage.

1 Drawing Sheet

The present invention relates to a new and distinct variety of rose plant of the floribunda class which was originated by me by crossing 'JACdew' (U.S. Plant Pat. No. 5,122), with 'HARrooney' (U.S. Plant Pat. No. 5,582).

The primary objective of this breeding was to produce a new rose variety having the vigorous growth, disease resistant foliage and abundant flowers of the female parent combined with the fragrance, compact growth and large individual flowers of the male parent. The objective was substantially achieved, along with other desirable improvements, as evidenced by the following unique combination of characteristics that are outstanding in the new variety and that distinguish it from its parents, as well as from all other varieties of which I am aware:

1. Strong fragrance;
2. Vigorous growth;
3. Disease resistant foliage;
4. Large flowers;
5. Compact plant habit.

Asexual reproduction of this new variety by budding, as performed at Wasco, Calif., shows that the foregoing and all other charactertistics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACdew' (U.S. Plant Pat. No. 5,122).

*Pollen parent.*—'HARrooney' (U.S. Plant Pat. No. 5,582).

Classification:

*Botanical.*—Rosa hybrida.

*Commercial.*—Floribunda.

FLOWER

Observations made from specimens grown in a garden environment at Somis, Calif., from March, 1996 to October, 1997.

Blooming habit: Continuous.

Bud:

*Size.*—1¼ to 1½" long when the petals start to unfurl.

*Form.*—The bud form is globular.

*Color.*—When sepals first divide, but color is Red Group 36C. When half blown, the uper sides of the petals are Red Group 36C and the lower sides of the petals are Red Group 36C.

*Sepals.*—Color: Green Group 138B. Surface texture: Covered in fine hairs. There are three lighty appendaged sepals. There are two unappendated sepals with hairy edges.

*Receptacle.*—Color: Green Group 137C and often bronzy when exposed to sunlight. Shape: Funnel. Size: Medium (¼"×¼"). Surface: Smooth.

*Peduncle.*—Length: Short (2"). Surface: Prickly. Color: Medium green and bronzy. Strength: Stiff, erect.

Bloom:

*Size.*—Medium. Average open size is 3½ to 4".

*Borne.*—Singly and several together in clusters of 3 to 5 flowers, having a rounded shape.

*Stems.*—Short (10–12").

*Form.*—When first open: Bloom is cupped. Permanence: Outer petals curl back.

*Petalage.*—Number of petals under normal conditions: 40–45.

*Color.*—The upper sides of the petals are Red Group 36C. The reverse sides of the petals are Red Group 36C. The base of each petal has a fairly lareg (⅜" wide by ⅛" tall), Yellow Orange Group 21C half moon. The major color on the upper sides is Red Group 36C.

*Variegations.*—There are occasional darker pink blotches on the guard petals.

*Discoloration.*—No change through to petal drop at day six or seven.

*Fragrance.*—Srong.

Petals:

*Texture.*—Thick.

*Shape.*—Round.

*Form.*—Tips slightly recurved.

*Arrangement.*—Imbricated. Petaloids in the center are few.

*Persistence.*—Petals drop off cleanly before drying.

*Lastingness.*—On the plant: Fair (6–7 days). As a cut flower: Fair (8 days).

Reproductive Parts:

*Anthers.*—Size: Medium. Quantity: Many. Color: Yellow. Arrangement; Regular around styles.

*Filaments.*—Color: Yellow.
*Pollen.*—Color: Gold yellow.
*Styles.*—Color: Reddish.
*Stigmas.*—Color: Greenish white.

Plant:
*Form.*—Bush.
*Growth.*—Vigorous; upright; branching; compact: Height of mature plant is three to three and one half feet, which is two and one half to three feet.

Foliage:
*Number of leaflets on normal mid-stem leaves.*—Five.
*Size.*—Medium (5"×3").
*Quantity.*—Abundant.
*Color.*—New foliage: Upper and lower sides Greyed Red 178A. Quickly turns to green coloration of old foliage. Old foliage: Upper side: Green Group 136A. Lower side: Yellow Green Group 147B.

Leaflets:
*Shape.*—Broadly oval.
*Texture.*—Upper side: Leathery, glossy.
*Edge.*—Serrated.
*Serration.*—Single, small.
*Petiole rachis.*—Color: Green.
*Petiole underside.*—Smooth.
*Stipules.*—Medium, (½"), bearded.
*Disease resistance.*—Resistant to mildew and rust under normal growing conditions at Somis, Calif.

Wood:
*New wood.*—Color: Reddish, quickly turning green. Bark: Smooth.
*Old wood.*—Color: Green. Bark: Smooth.

Prickles:
*Quantity.*—One main canes from base: Ordinary. On laterals from main caanes: Ordinary.
*Form.*—Medium: hooked downward.
*Color when young.*—Red.

Small prickles:
*Quantity.*—On main stalks: Few to None on main stalks. On laterals: None on laterals.

I claim:

1. A new and distinct rose plant of the floribunda class, substantially as herein shown and described, characterized particularly as to novelty by the unique combination of its large flowers having strong fragrance, vigorous growth, compact plant habit and disease resistant foliage.

* * * * *

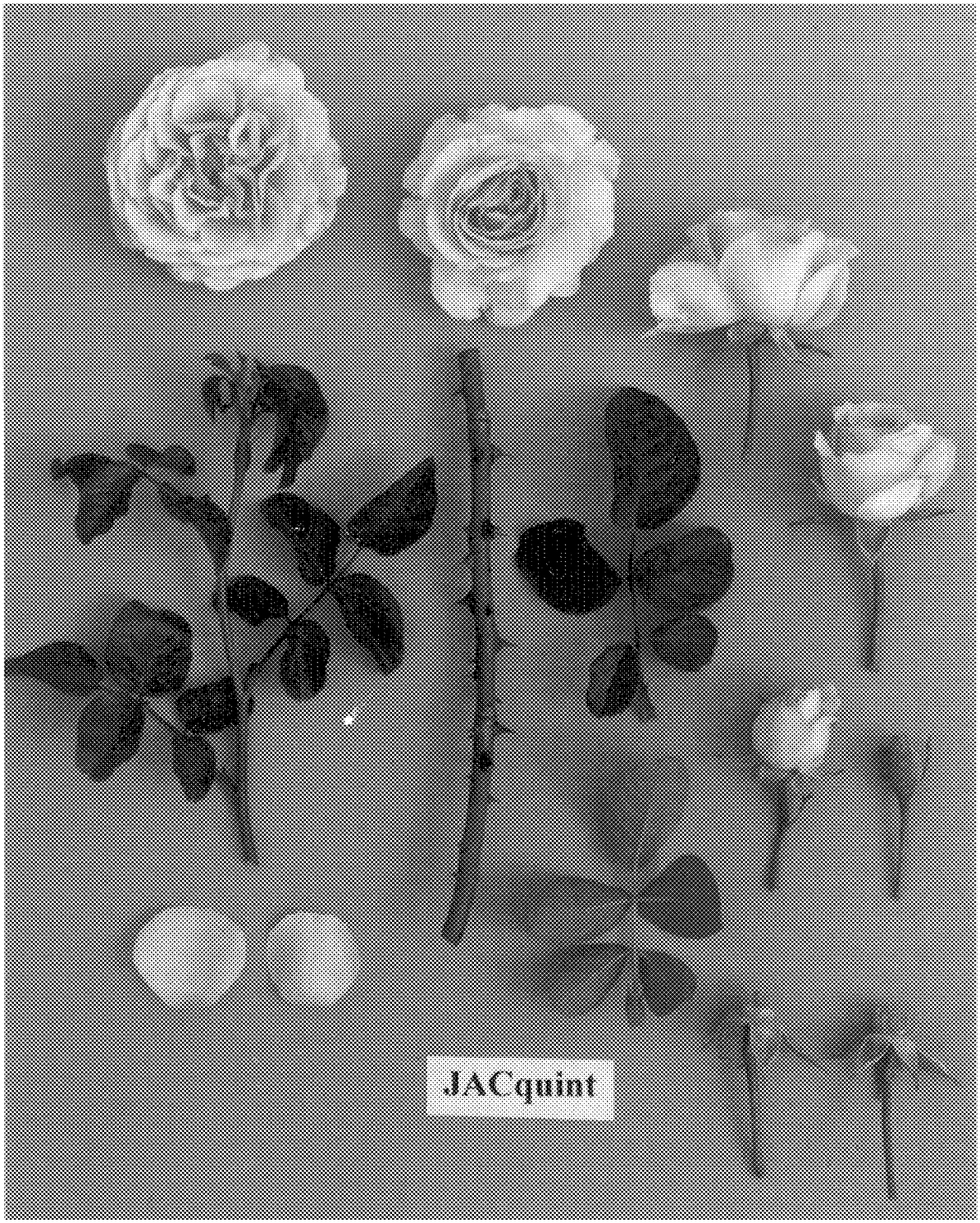
JACquint

UNITED STATES PATENT AND TRADEMARK OFFICE
CERTIFICATE OF CORRECTION

PATENT NO. : PP11,170

DATED : January 4, 2000

INVENTOR(S) : Keith W. Zary, Ph.D.

It is certified that errors appear in the above-identified patent and that said Letters Patent is hereby corrected as shown below:

In the Specification:

Col. 2, line 5, reads "but". It should read --bud--.
Col. 2, line 6, reads "uper". It should read --upper--.
Col. 2, line 10, reads "lighty". It should read --lightly--.
Col. 2, line 11, reads "unappendated". It should read --unappendaged--.
Col. 2, line 29, reads "lareg". It should read --large--.
Col. 2, line 37, reads "Srong". It should read --Strong--.
Col. 2, line 49, reads "Arrangement;". It should read --Arrangement:--.
Col. 3, line 9, reads "which". It should read --width--.
Col. 4, line 10, reads "One". It should read --On--.
Col. 4, line 11, reads "caanes". It should read --canes--.
Col. 4, line 12, reads "Medium: hooked". It should read --Medium; hooked--.
Col. 4, line 15, reads "stalks: Few to None". It should read --stalks: None--.

Signed and Sealed this

Twenty-ninth Day of May, 2001

*Attest:*

Nicholas P. Godici

NICHOLAS P. GODICI

*Attesting Officer*

*Acting Director of the United States Patent and Trademark Office*